United States Patent [19]

Agar et al.

[11] Patent Number: 5,175,316
[45] Date of Patent: Dec. 29, 1992

[54] CYCLIC PREPARATION OF CYCLOHEXENE OXIDE, CYCLOHEXANOL AND CYCLOHEXANONE

[75] Inventors: David Agar, Rimbach; Paul-Michael Bever, Mannheim; Hans H. Schuster, Erpolzheim; Gerald Neubauer, Weinheim, all of Fed. Rep. of Germany

[73] Assignee: BASF Aktiengesellschaft, Ludwigshafen, Fed. Rep. of Germany

[21] Appl. No.: 833,173

[22] Filed: Feb. 10, 1992

[30] Foreign Application Priority Data

Feb. 14, 1991 [DE] Fed. Rep. of Germany ....... 4104419

[51] Int. Cl.⁵ ................. C07D 301/19; C07D 303/04; C07C 27/12; C07C 35/08
[52] U.S. Cl. ................................... 549/529; 568/357; 568/577; 568/836
[58] Field of Search .......................................... 549/529

[56] References Cited

U.S. PATENT DOCUMENTS 3,870,729  3/1975  Bost et al. .................. 260/348.5
4,814,511  3/1989  Neubauer et al. ................ 549/529

FOREIGN PATENT DOCUMENTS 135718  6/1986  European Pat. Off. .
092867  7/1986  European Pat. Off. .
2404950  8/1974  Fed. Rep. of Germany .
3636056  4/1988  Fed. Rep. of Germany .
26923  8/1971  Japan .................................. 549/529

*Primary Examiner*—Joseph E. Evans
*Attorney, Agent, or Firm*—Keil & Weinkauf

[57] ABSTRACT

The preparation of cyclohexene oxide, cyclohexanol and cyclohexanone involves
  a) oxidizing cyclohexane using a gas containing molecular oxygen to form cyclohexyl hydroperoxide, cyclohexanol and cyclohexanone,
  b) jointly separating the mixture from a) and c) by distillation, and
  c) reaction of the cyclohexyl hydroperoxide fraction from b) with cyclohexene in the presence of a transition-metal compound from group 4 to 6, forming cyclohexene oxide, and separating the product mixture in b).

4 Claims, No Drawings

CYCLIC PREPARATION OF CYCLOHEXENE OXIDE, CYCLOHEXANOL AND CYCLOHEXANONE

EP-A 92 867 discloses treating cyclohexyl hydroperoxide-containing reaction mixtures from the oxidation of cyclohexane with aqueous solutions of alkali metal hydroxides, possibly containing catalytically active metal salts, in order to convert the cyclohexyl hydroperoxide present in the reaction mixture into cyclohexanol and cyclohexanone. This process has the disadvantage that considerable amounts of alkali metal hydroxides must be used and disposed of, and in addition considerable amounts of cyclohexanone and/or cyclohexanol are lost to formation of high-boiling components.

DE-A 24 04 950 describes a process for the preparation of cyclohexene oxide by reacting cyclohexene with cyclohexyl hydroperoxide in the presence of soluble titanium catalysts and in the presence of phosphoric acid esters. However, there is no indication of how this process can be combined with the process for the preparation of cyclohexyl hydroperoxide.

DE-A 36 36 056 discloses that cyclohexyl hydroperoxide obtained by oxidizing cyclohexane can be reacted, in the solution produced on oxidation, with mixtures of cyclohexene and cyclohexane in the presence of soluble metal catalysts from subgroup 4 to 6 of the periodic table, and the cyclohexene oxide present in the solution can subsequently be hydrogenated to give cyclohexanol. It is noteworthy that cyclohexene is used in excess, relative to the cyclohexyl hydroperoxide, which is also hydrogenated. There is no indication of how to reduce the unavoidable formation of cyclohexane.

It is therefore an object of the present invention to provide a cyclic process for the preparation of cyclohexene oxide, cyclohexanol and cyclohexanone in which a very small amount of non-useful by products is produced, optimum integration of cyclohexane oxidation and cyclohexene epoxidation is achieved, and, in addition, the work-up complexity is minimized.

We have found that this object is achieved by a cyclic process for the preparation of cyclohexene oxide, cyclohexanol and cyclohexanone which includes the following steps:

a) preparation of a mixture essentially comprising cyclohexyl hydroperoxide, cyclohexanol, cyclohexanone and cyclohexane by oxidizing cyclohexane using molecular oxygen or a gas containing molecular oxygen at from 130° to 200° C. and at from 5 to 125 bar in the liquid phase, b) joint distillative separation of the mixture from step a) and an epoxidation mixture produced in step c) and containing cyclohexene oxide, to give the following fractions $b_1$) a fraction which essentially comprises cyclohexane and cyclohexene and is recycled into step a) after hydrogenation, $b_2$) a fraction which essentially comprises cyclohexene oxide, $b_3$) a mixture which essentially comprises cyclohexanol and cyclohexanone, and $b_4$) a fraction which essentially comprises cyclohexyl peroxide, cyclohexanol, cyclohexanone and catalyst, and c) reaction of the mixture obtained as fraction $b_4$) and containing cyclohexyl hydroperoxide with cyclohexene in a mixture with cyclohexane at elevated temperature in the presence of transition-metal compounds from group 4 to 6 of the periodic table, to give an epoxidation mixture which essentially comprises cyclohexene oxide, cyclohexanol, cyclohexanone, cyclohexene, cyclohexane and catalyst and is separated by distillation in step b) together with the mixture from a).

The novel process has the advantage that it is possible to prepare cyclohexyl hydroperoxide, alongside cyclohexanol and cyclohexanone, and cyclohexene oxide by reacting cyclohexene with cyclohexyl hydroperoxide in a combined cyclic process with joint work-up. The novel process has the further advantage that the catalysts used are recycled and in addition the formation of non-useful byproducts is minimized. In addition, complex separation of cyclohexene and cyclohexane is not necessary. Furthermore, it is possible to produce up to 2 mol of cyclohexanol per mol of cyclohexyl hydroperoxide.

In step a), a mixture essentially comprising cyclohexyl hydroperoxide, cyclohexanol, cyclohexanone and cyclohexane is prepared by oxidizing cyclohexane using molecular oxygen or a gas containing molecular oxygen at from 130° to 200° C and at from 5 to 125 bar in the liquid phase. If necessary, a catalyst, such as a cobalt salt, can also be used. The oxidation is advantageously carried out to a conversion of from 2 to 8% by weight, based on the cyclohexane employed. The pressure and temperature are matched to one another so that at any point in time the reaction is taking place in the liquid phase.

The oxidation of cyclohexane is carried out by a suitable process, for example in a vertical reaction zone containing perforated metal sheets at equal separations. The sheets advantageously have a free cross-section of 3 to 20%. Nozzles are arranged above each perforated sheet in a uniform distribution over the cross-section and are used to feed in the oxygen-containing gas, in particular air. Cyclohexane is passed through the reaction zone from bottom to top, and a gas containing molecular oxygen, for example containing from 5 to 30% by volume of oxygen, advantageously air, is simultaneously introduced through each nozzle aperture. The amounts of molecular oxygen-containing gas and cyclohexane introduced are balanced to one another in such a manner that the offgas leaving the reaction zone contains not more than from 0.1 to 1.5% by volume of molecular oxygen. A suitable process is described, for example, in EP-B 135 718. Before further processing, the solution obtained may also be enriched in cyclohexyl hydroperoxide by removing some of the cyclohexane by distillation, for example by decompression distillation.

Typical reaction mixtures contain, for example, from 0.5 to 5.0% by weight of cyclohexyl hydroperoxide, from 0.1 to 2.5% by weight of cyclohexanol and from 0.1 to 1.5% by weight of cyclohexanone in addition to cyclohexane and byproducts, such as esters and carboxylic acids. Such reaction mixtures are advantageously washed with water and/or aqueous alkali metal carbonate solutions before further treatment.

In step b), the cyclohexyl hydroperoxide-containing mixture from step a) and a cyclohexene oxide-containing epoxidation mixture which is produced in step c) and essentially comprises cyclohexanol, cyclohexanone, cyclohexene oxide, cyclohexene, cyclohexane and catalyst are jointly separated by distillation. The mixtures from step a) and step c) to be distilled are advantageously mixed before introduction into the column. On distillation, the following fractions are separated:

b₁) a fraction which essentially comprises cyclohexane and cyclohexene. A typical mixture contains, for example, from 0.1 to 5% by weight of cyclohexene in addition to cyclohexane. The cyclohexene-containing fraction is hydrogenated, and the cyclohexane obtained is recycled into step a) as a starting compound for the oxidation. The hydrogenation is carried out in the presence of a hydrogenation catalyst, in particular a metal from group 8 of the periodic table, for example cobalt, nickel or a noble metal, such as palladium or platinum, at from 100° to 200° C. under superatmospheric pressure, for example at from 10 to 130 bar, expediently in the liquid phase.

Fraction b₂) essentially comprises cyclohexene oxide containing small amounts of impurities, such as cyclohexane, cyclohexene, cyclohexanol, cyclohexanone and cyclohexyl hydroperoxide.

Fraction b₃) is a mixture which essentially comprises cyclohexanol and cyclohexanone. A typical mixture contains, for example, from 50 to 95% by weight of cyclohexanol, from 5 to 50% by weight of cyclohexanone and up to 2% by weight of impurities.

The other fraction b₄) is a mixture which essentially comprises cyclohexyl hydroperoxide, cyclohexanol, cyclohexanone and catalyst. The catalyst is described in greater detail below. A typical mixture contains, for example, from 10 to 20% by weight of cyclohexyl hydroperoxide in addition to cyclohexanol and cyclohexanone and from 0.01 to 5% by weight of catalyst, calculated as the metal and based on cyclohexyl hydroperoxide.

In step c), the cyclohexyl hydroperoxide-containing fraction b₄) is contacted with cyclohexene as a mixture with cyclohexane, and cyclohexyl hydroperoxide is reacted with cyclohexene to form cyclohexene oxide and cyclohexanol. Cyclohexyl hydroperoxide is advantageously used in excess, based on cyclohexene. The ratio between cyclohexene and cyclohexyl hydroperoxide is advantageously from 0.7 to 1. The reaction is carried out at elevated temperature, advantageously at from 70° to 150° C., in particular at from 90° to 140° C., and in the liquid phase. The residence time is advantageously from 15 to 120 minutes, in particular from 30 to 100 minutes. The pressure is selected so that the reaction mixture does not form a gas phase and is always in a liquid phase.

The reaction is carried out in the presence of a transition-metal compound from group 4 to 6 of the periodic table. The compound used is advantageously soluble in cyclohexane. Examples of suitable metals are titanium, zirconium, vanadium, niobium, tantalum, chromium, molybdenum and tungsten. Examples of suitable compounds are acetylacetonates or salts with higher fatty acids, for example having from 8 to 18 carbon atoms, such as 2-ethylhexanoic acid, undecanoic acid, stearic acid, palmitic acid or naphthenates. Particular preference is given to compounds of molybdenum, titanium, vanadium or tungsten, with molybdenum compounds having achieved particular importance. From 0.1 to 2 mmol of the catalyst, calculated as the metal, are advantageously used per mol of cyclohexyl hydroperoxide.

Cyclohexene is used as a mixture with cyclohexane. A typical mixture contains, for example, from 10 to 30% by weight of cyclohexene. The catalyst is replenished by adding fresh catalyst, expediently in dissolved form, to step c) together with the cyclohexene and cyclohexane.

An epoxidation mixture is obtained which essentially comprises cyclohexene oxide, cyclohexanol, cyclohexanone, cyclohexene, dissolved catalyst and cyclohexane. A typical mixture contains, for example, from 0.1 to 1% by weight of cyclohexene, from 5 to 20% by weight of cyclohexanol, from 1 to 15% by weight of cyclohexanone, from 1 to 10% by weight of cyclohexyl hydroperoxide and from 50 to 90% by weight of cyclohexane. The resultant mixture is separated by distillation in step b) together with the oxidation mixture from step a).

The distillation of the mixtures from steps a) and b) is expediently carried out in two columns. For example, the mixture to be distilled is fed to the central part of the first column, and a mixture of cyclohexane and cyclohexene is taken off at the top of the column, while the cyclohexyl hydroperoxide-containing fraction b₄) is taken off at the bottom of the column. Cyclohexene oxide (fraction b₂) and the mixture of cyclohexanol and cyclohexanone (fraction b₃) are taken off in a bypass-connected column. It is advantageous to ensure that a temperature of 110° C. is not exceeded at the bottom of the first column. The distillation is generally carried out under reduced pressure, for example at from 50 to 300 mbar. The cyclohexyl hydroperoxide is advantageously separated off after a maximum residence time of 120 minutes, preferably from 10 to 60 minutes.

The cyclohexene oxide obtained in this way can be hydrogenated in the presence of a noble-metal catalyst, for example palladium, to give cyclohexanol, which can then be used together with the mixture of cyclohexanol and cyclohexanone to prepare fiber precursors.

The process of the invention is illustrated with reference to the Examples below.

EXAMPLE

A mixture of the following composition was employed for the epoxidation:

| A) Cyclohexene: | 6.8% by weight |
|---|---|
| Cyclohexene oxide: | 0.03% by weight |
| Cyclohexanone: | 0.93% by weight |
| Cyclohexanol: | 1.97% by weight |
| Cyclohexyl hydroperoxide: | 11.6% by weight |

The solution contained 0.5 mmol of Mo/mol of CHHP as catalyst. It was reacted in a reactor at 110° C. and a residence time of 60 minutes. After the reaction, the product mixture contained:

| B) Cyclohexene: | 0.39% by weight |
|---|---|
| Cyclohexene oxide: | 5.78% by weight |
| Cyclohexanone: | 2.03% by weight |
| Cyclohexanol: | 9.35% by weight |
| Cyclohexyl hydroperoxide: | 0.91% by weight |

Crude oxidate from the oxidation of cyclohexane was added to the resultant mixture B, and the mixture was then evaporated under reduced pressure at 90° C. in a thinfilm evaporator. The bottom product had the following composition:

C) 
| | |
|---|---|
| Cyclohexene: | 0.05% by weight |
| Cyclohexene oxide: | 2.02% by weight |
| Cyclohexanone: | 2.14% by weight |
| Cyclohexanol: | 8.06% by weight |
| Cyclohexyl hydroperoxide: | 12.7% by weight |

Sufficient cyclohexene to give a cyclohexyl hydroperoxide:cyclohexene ratio of about 0.7 mol/mol was added to this bottom product before it was recycled into the epoxidation reactor. The starting material before epoxidation had the following composition:

| | |
|---|---|
| Cyclohexene: | 4.69% by weight |
| Cyclohexene oxide: | 1.68% by weight |
| Cyclohexanone: | 1.96% by weight |
| Cyclohexanol: | 7.87% by weight |
| Cyclohexyl hydroperoxide: | 10.4% by weight |

The reaction conditions correspond to those for A. The product obtained had the composition:

| | |
|---|---|
| Cyclohexene: | 0.62% by weight |
| Cyclohexene oxide: | 5.45% by weight |
| Cyclohexanone: | 3.44% by weight |
| Cyclohexanol: | 13.2% by weight |
| Cyclohexyl hydroperoxide: | 2.08% by weight |

We claim:

1. A cyclic process for the preparation of cyclohexene oxide, cyclohexanol and cyclohexanone which includes the following steps:
   a) preparation of a mixture essentially comprising cyclohexyl hydroperoxide, cyclohexanol, cyclohexanone and cyclohexane by oxidizing cyclohexane using molecular oxygen or a gas containing molecular oxygen at from 130° to 200° C. and at from 5 to 125 bar in the liquid phase,
   b) joint distillative separation of the mixture from step a) and an epoxidation mixture produced in step c) and containing cyclohexene oxide, to give the following fractions
      $b_1$) a fraction which essentially comprises cyclohexane and cyclohexene and is recycled into step a) after hydrogenation,
      $b_2$) a fraction which essentially comprises cyclohexene oxide,
      $b_3$) a mixture which essentially comprises cyclohexanol and cyclohexanone, and
      $b_4$) a mixture which essentially comprises cyclohexyl hydroperoxide, cyclohexanol, cyclohexanone and catalyst,
   and
   c) reaction of the mixture obtained as fraction $b_4$) and containing cyclohexyl hydroperoxide with cyclohexene in a mixture with cyclohexane at elevated temperature in the presence of transition-metal compounds from group 4 to 6 of the periodic table, to give an epoxidation mixture which essentially comprises cyclohexene oxide, cyclohexanol, cyclohexanone, cyclohexene, cyclohexane and catalyst and is separated by distillation in step b) together with the mixture from a).

2. A process as claimed in claim 1, wherein molybdenum compounds which are soluble in cyclohexane are used.

3. A process as claimed in claim 1, wherein the separation of the mixture containing cyclohexyl peroxide is carried out at a maximum residence time of 120 minutes.

4. A process as claimed in claim 1, wherein a molar ratio between cyclohexene and cyclohexyl hydroperoxide of from 0.7 to 1 is maintained.

* * * * *